(12) United States Patent
Brady et al.

(10) Patent No.: US 11,094,405 B2
(45) Date of Patent: Aug. 17, 2021

(54) COGNITIVE CARE PLAN RECOMMENDATION SYSTEM

(71) Applicant: INTERNATIONAL BUSINESS MACHINES CORPORATION, Armonk, NY (US)

(72) Inventors: Simon Brady, Dublin (IE); John Leonard, Dublin (IE); Shane Dalton, Dublin (IE); Clea Anne Zolotow, Key West, FL (US); John Valentine Delaney, Kildalkey (IE); Patrick Arthur Fagan, Naas (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 309 days.

(21) Appl. No.: 16/262,334

(22) Filed: Jan. 30, 2019

(65) Prior Publication Data

US 2020/0243172 A1    Jul. 30, 2020

(51) Int. Cl.
*G16H 10/60* (2018.01)
*G06F 16/903* (2019.01)

(52) U.S. Cl.
CPC ....... *G16H 10/60* (2018.01); *G06F 16/90344* (2019.01)

(58) Field of Classification Search
CPC ........ G16H 10/60; G16H 50/20; G16H 40/20; G06F 16/90344; G06F 16/90332
See application file for complete search history.

(56) References Cited

U.S. PATENT DOCUMENTS

| | | | |
|---|---|---|---|
| 2006/0095521 A1* | 5/2006 | Patinkin | H04L 51/12 709/206 |
| 2008/0077570 A1* | 3/2008 | Tang | G06F 16/3346 |
| 2014/0350961 A1 | 11/2014 | Csurka et al. | |
| 2014/0358581 A1 | 12/2014 | Sudharsan | |
| 2016/0140300 A1* | 5/2016 | Purdie | A61N 5/103 705/2 |
| 2016/0335397 A1 | 11/2016 | Blum et al. | |
| 2017/0177812 A1 | 6/2017 | Sjolund | |

* cited by examiner

*Primary Examiner* — Linh Giang Le
(74) *Attorney, Agent, or Firm* — Scott S. Dobson, Esq.; Wayne F. Reinke, Esq.; Heslin Rothenberg Farley & Mesiti P.C.

(57) ABSTRACT

Finding care plan(s) matching desired aspects includes receiving a selection of a model care plan from a user; generating a feature hash vector representing the model care plan, resulting in a model feature hash vector; comparing feature hash vectors of existing care plans to the model feature hash vector to find care plan(s) best matching the desired aspect(s) of a user, resulting in best match(es); and providing one or more care plan recommendation(s) to the user based on the best match(es).

20 Claims, 5 Drawing Sheets

COGNITIVE CARE PLAN RECOMMENDATION SYSTEM

BACKGROUND

A Care Management System may contain many thousands of Care Plans. It can be difficult and expensive to query the system as to what sort of Care Plans are successful or not successful. Existing solutions rely on data warehousing which is often complex to set up and expensive and slow to run. These solutions are often not "agile" or easy to reconfigure.

SUMMARY

Shortcomings of the prior art are overcome and additional advantages are provided through the provision, in one aspect, of a computer-implemented method of finding one or more care plan matching desired aspects. The method includes: receiving a selection of a model care plan from a user; generating a feature hash vector representing the model care plan, resulting in a model feature hash vector; comparing feature hash vectors of a plurality of existing care plans to the model feature hash vector to find one or more care plan best matching one or more desired aspect of the user, resulting in one or more best match; and providing one or more care plan recommendation to the user based on the one or more best match.

In another aspect, a system for scheduling a meeting may be provided. The system may include, for example, memory (ies), at least one processor in communication with the memory(ies). The memory(ies) include program instructions executable by the one or more processor to perform a method. The method may include, for example: receiving a selection of a model care plan from a user; generating a feature hash vector representing the model care plan, resulting in a model feature hash vector; comparing feature hash vectors of a plurality of existing care plans to the model feature hash vector to find one or more care plan best matching one or more desired aspect of the user, resulting in one or more best match; and providing one or more care plan recommendation to the user based on the one or more best match.

In a further aspect, a computer program product may be provided. The computer program product may include a computer readable storage medium readable by a processor and storing instructions executable by the processor for finding one or more care plan matching desired aspects. The method may include, for example: receiving a selection of a model care plan from a user; generating a feature hash vector representing the model care plan, resulting in a model feature hash vector; comparing feature hash vectors of a plurality of existing care plans to the model feature hash vector to find one or more care plan best matching one or more desired aspect of the user, resulting in one or more best match; and providing one or more care plan recommendation to the user based on the one or more best match.

Services relating to one or more aspects of this disclosure are also described and may be claimed herein.

Additional features and advantages are realized through the techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

One or more aspects of this disclosure relate, in general, to developing plans to assist people. More particularly, one or more aspects of this disclosure relate to a cognitive care plan recommendation engine. This system will allow Care Managers to: choose care plans from within the care management system that they regard as exemplars for any arbitrary criteria, good or bad; tag these care plans as model care plans within the care management system; and ask the care management system to generate a list of other existing care plans that are similar to these model care plans.

As used herein, the term "care plan" refers to a plan centered around one person with one or more central goal and activities structured to achieve the central goal(s). The activities can include any activity that advances or supports the central goal(s), for example, medical appointment(s), counseling, exercise regimen, physical therapy, pharmaceuticals, etc. When the central goal(s) are achieved, the care plan is considered to be a success and may be referred to as a "model" care plan.

Figure 1:
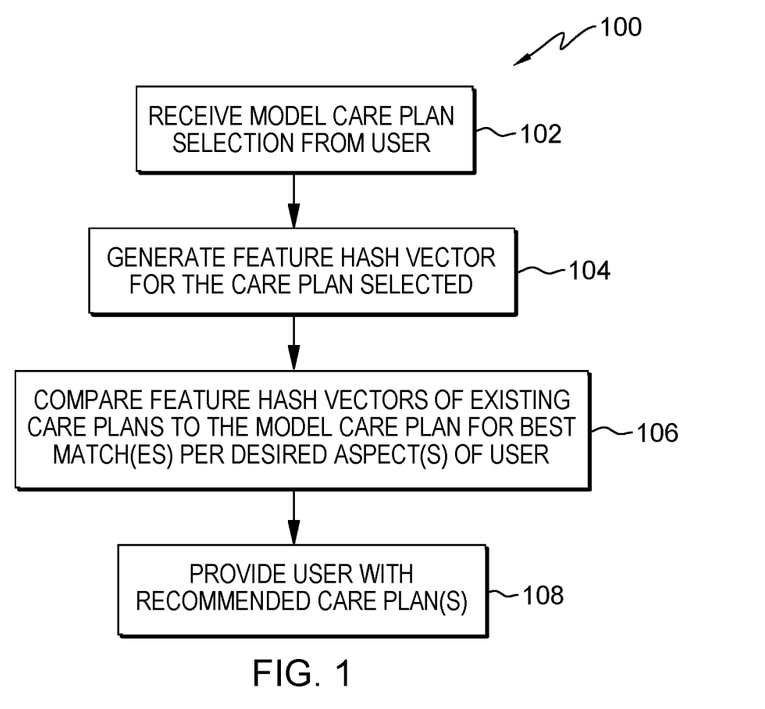
FIG. 1 is a flow diagram for one example of a computer-implemented method of cognitively recommending a care plan, in accordance with one or more aspects of the present disclosure.

FIG. 1 is a flow diagram 100 for one example of a computer-implemented method of cognitively recommending a care plan, in accordance with one or more aspects of the present disclosure. The computer-implemented method includes, for example, receiving 102, by a data processing system, a selection of a model care plan from a user and generating 104, by the data processing system, a feature hash vector representing the selected model care plan, resulting in a model feature hash vector. The data processing system then compares 106 feature hast vectors of existing care plans to the model feature hash vector to find care plan(s) best matching one or more desired aspect of the user, resulting in one or more best match. In one embodiment, a comparison of care plans can be done using, for example, a cosine similarity function. Based on results of the comparison, the data processing system provides one or more care plan recommendations to the user based on the one or more best match.

Figure 2:
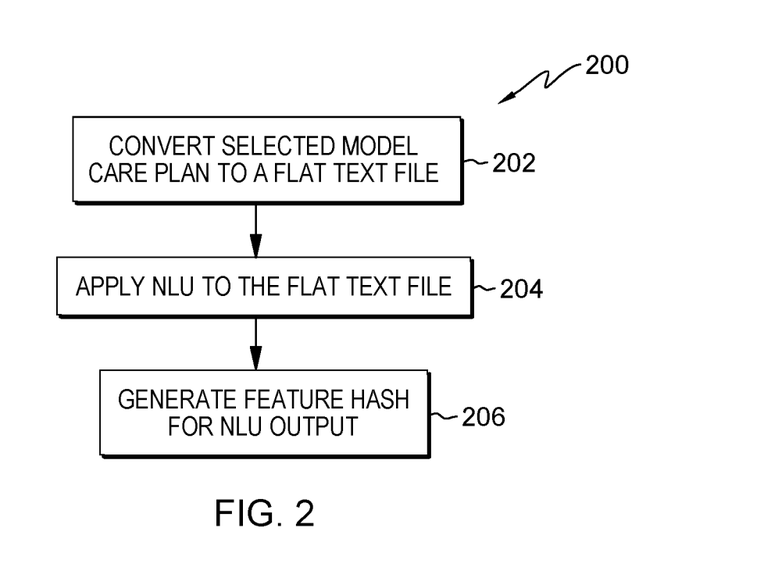
FIG. 2 is a flow diagram for one example of generating a feature hash vector for the care plan selected by the user, in accordance with one or more aspects of the present disclosure.

FIG. 2 is a flow diagram 200 for one example of generating a model feature hash vector for the model care plan selected by the user, in accordance with one or more aspects of the present disclosure. The care plan is first converted 202 to a flat text file by the data processing system. Natural Language Understanding (NLU) is then applied 204 to the flat text file by the data processing system. A feature hash is then generated 206 from results of applying NLU to the flat text file.

The present disclosure utilizes a technique known as feature hashing. In a typical document classification task, the input to the machine learning algorithm (both during learning and classification) is free text. From this, a bag of words (BOW) representation is constructed: the individual tokens are extracted and counted, and each distinct token in the training set defines a feature (independent variable) of each of the documents in both the training and test sets.

Machine learning algorithms, however, are typically defined in terms of numerical vectors. Therefore, the bags of words for a set of documents is regarded as a term-document matrix where each row is a single document, and each column is a single feature/word; the entry j in such a matrix captures the frequency (or weight) of the j'th term of the vocabulary in document i. (An alternative convention swaps the rows and columns of the matrix, but this difference is immaterial.) Typically, these vectors are extremely sparse—according to Zipf's law.

The common approach is to construct, at learning time or prior to that, a dictionary representation of the vocabulary of the training set, and use that to map words to indices. The problem with this process is that such dictionaries take up a large amount of storage space and grow in size as the training set grows.

Instead of maintaining a dictionary, a feature vectorizer that uses hashing can build a vector of a pre-defined length by applying a hash function h to the features (e.g., words), then using the hash values directly as feature indices and updating the resulting vector at those indices. Here, we assume that feature actually means feature vector.

Thus, if our feature vector is ["cat," "dog," "cat"] and hash function is hash($x_f$)=1 if $x_f$ is "cat" and 2 if $x_f$ is "dog." Let us take the output feature vector dimension (N) to be 4. Then output x will be [0,2,1,0]. It has been suggested that a second, single-bit output hash function be used to determine the sign of the update value, to counter the effect of hash collisions. If such a hash function is used, the algorithm becomes function hashing_vectorizer(features: array of string, N: integer):

```
x:=new vector[N]
for f in features:
  h:=hash(f)
  idx:=h mod N
  if ξ(f)==1:
    x[idx]+=1
  else:
    x[idx]-=1
return x
```

The above pseudo code actually converts each sample into a vector. An optimized version would instead only generate a stream of (h,ξ) pairs and let the learning and prediction algorithms consume such streams; a linear model can then be implemented as a single hash table representing the coefficient vector.

Cosine similarity is a measure of similarity between two non-zero vectors of an inner product space that measures the cosine of the angle between them. The cosine of 0° is 1, and it is less than 1 for any angle in the interval (0,π) radians. It is thus a judgment of orientation and not magnitude: two vectors with the same orientation have a cosine similarity of 1, two vectors oriented at 90° relative to each other have a similarity of 0, and two vectors diametrically opposed have a similarity of −1, independent of their magnitude. The cosine similarity is particularly used in positive space, where the outcome is neatly bounded in [0,1]. The name derives from the term "direction cosine": in this case, unit vectors are maximally "similar" if they are parallel and maximally "dissimilar" if they are orthogonal (perpendicular). This is analogous to the cosine, which is unity (maximum value) when the segments subtend a zero angle and zero (uncorrelated) when the segments are perpendicular.

These bounds apply for any number of dimensions, and the cosine similarity is most commonly used in high-dimensional positive spaces. For example, in information retrieval and text mining, each term is notionally assigned a different dimension and a document is characterized by a vector where the value in each dimension corresponds to the number of times the term appears in the document. Cosine similarity then gives a useful measure of how similar two documents are likely to be in terms of their subject matter.

The technique is also used to measure cohesion within clusters in the field of data mining.

One advantage of cosine similarity is its low-complexity, especially for sparse vectors: only the non-zero dimensions need to be considered.

Figure 3:
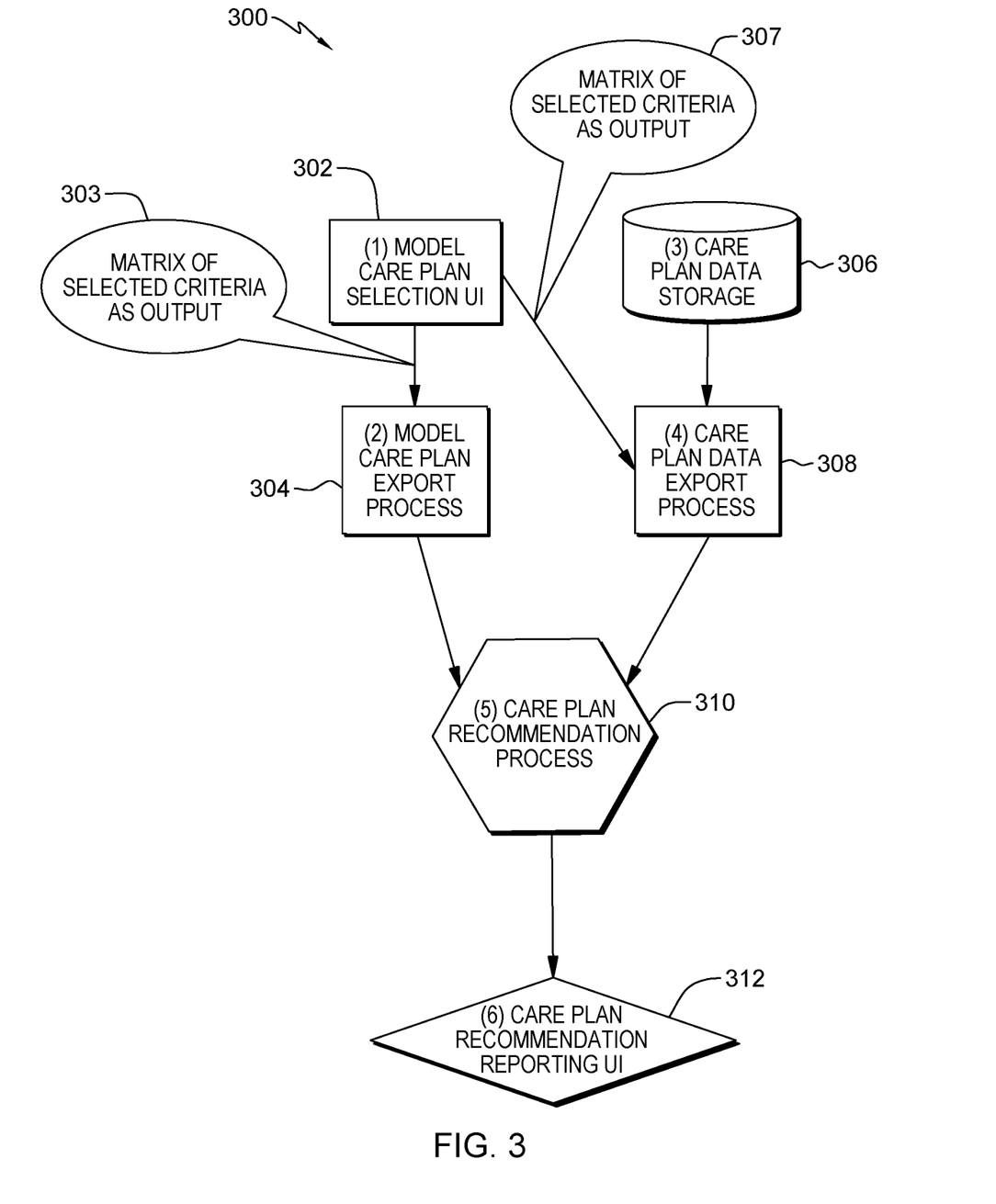
FIG. 3 is a block diagram of a system for cognitively recommending a care plan, in accordance with one or more aspects of the present disclosure.

FIG. 3 is a modified block diagram 300 of a cognitive care plan recommendation system, in accordance with one or more aspects of the present disclosure. The invention includes the following components, for example, a user interface component 302 to allow the user (e.g., a Care Manager) to choose and flag a model care plan. This user interface will output a matrix of selected criteria 303. Component 304 is for processing a model care plan into a feature hash. This component will take the matrix of all identified criteria from component 302 and export the model care plan as a feature hash. Care plan data can be stored in a storage component 306, such as, for example, a database. Component 308 is for processing general care plan data, which takes the matrix of all identified criteria identified in component 302 and exports 307 a selection of care plans from storage component 306 using this matrix. Comparison component 310 compares the outputs of components 304 and 308 using a care plan recommendation score, as described herein. Reporting user interface component 312 allows the Care Manager to view the results.

In one example, a care plan is created for a person who lost their job and then their home to fire (without insurance) and, as a result, needs housing. One goal for a care plan may include finding temporary and permanent housing, finding a job and developing a health care plan. The care plan may include, for example, assisting the person to apply for aid (federal and/or state and/or local), working with legal professionals to review legal documents, helping the person find work and helping the person to address health issues.

In another example, a care plan is created for a person in court for a crime related to their drug addiction. The goal(s) for this person may include, for example, overcoming the addiction and finding work. The care plan may include, for example, a program of drug testing, engagement with a parole officer, training to find work and/or putting together an education plan.

In still another example, a care plan is created for someone diagnosed with diabetes. One goal for a care plan can include, for example, getting the diabetes under control. Such a care plan may include, for example, education and planning regarding food and drink, an exercise regimen, a schedule of testing and education regarding monitoring their blood sugar.

Each of the care plan examples above are created around goals for the individual.

A Care Manager selects a model care plan to provide to the care management system disclosed herein based on one or more desired aspect, which could include everything from the staff involved to medical and social engagement. A model feature hash vector is generated for the model care plan. The model care plan selected to begin the search could be an existing care plan or an empty care plan with specific criteria (i.e., the desired aspect(s)). Care plan data may be exported in a flat text file format for processing, described in more detail below, and may be processed using Natural Language Understanding (NLU) tools. Feature hashing is used to turn the flattened care plan data into simple vectors. A feature hash is a fast and efficient way to vectorize multi-dimensional data. The resulting feature hash vectors can be stored and queried as with any other data. The care management system compares feature hast vectors of other care plans to that of the model care plan for all available features using, for example, a cosine similarity function. The output can then be filtered, along with other arbitrary attributes added back into the reporting for weighting purposes. The attributes could be anything from geographic data to specific medical conditions. A care plan recommendation score is attached to each result based on the cosine similarity function and the weighting factors added by the Care Manager.

One or more of these care plan may be tagged as model care plans in the care management system. In addition, extra text attributes can be added to the model care plans. In one embodiment, all care plan data is exported to a flat text format. This data is tagged and stemmed using NLU tools. Process data is converted to feature hash vectors. Feature hash vectors are compared to model care plans using a cosine similarity function. Care plan data is filtered on returned cosine similarity values. This returned data can also be filtered on other attributes as required.

The care management system would be extremely fast, given the use of feature hashes and cosine similarity function, and resource friendly compared to a standard data warehouse system. Feature hashes are fast and efficient. They can reduce exceptionally complex data to simple vectors without any performance hit. As feature hashes do not retain any of the original data, there is no concern about storage of personal health information. However, these feature hashes can still be used for comparison of care plans. As feature vectors do not remove any implicit feature data from the care plan, the system can compare across all of the data within a given care plan, from medical notes to diagnosis. Extra text-based data may be pushed into the system to be vectorized also, thus allowing very specific care plans to be created without any technical assistance for Care Managers. Once care plan data have been vectorized, it can then be stored in the same structure as any other data (e.g., SQL structure). This allows the recommendation system to be queried as simply as any other existing data, thereby making the system agile and useful to Care Managers. Allowing a Care Manager to add arbitrary weighting factors to the final care plan recommendation score makes the system much more flexible and agile. These weighting factors could be changed and queried on the fly without regenerating feature hashes, allowing extra querying without any extra data processing. It is envisaged that this care plan modeling capability could be easily implemented in an easy-to-use web based interface making it easy for non-technical staff to use.

There is no known system that allows Care Managers to simply model a care plan and compare this model to existing care plans for ranking and recommendations. In that regard, assigning a care plan recommendation score based on the cosine similarity function and the weighting factors added by the Care Manager may be utilized. Medical data alongside medical notes and case observations can be converted to feature hashes, i.e., compressing all the information pertaining to a care plan, may be used. Using feature hashes to allow comparison of medical data without needing to store personal health information is also unique.

The following outlines one example of a Care Manager using the system disclosed herein to find the best care plan for a new patient who suffers from dementia and also has existing anxiety issues and high blood pressure. In one embodiment, the Care Manager may create a new empty care plan and select the following criteria: medical diagnosis of dementia and high blood pressure; and the geographic locality of the patient. In another embodiment, the Care Manager could choose an existing care plan. The Care Manager may also add extra weighting for the keyword "anxiety" and for care plans that have successful outcomes. Successful outcomes for care plans could be captured in many ways, depending on the system, but herein it is assumed the existence of a simple feature called a "goal" which can be successful or unsuccessful. This set of criteria is designated a model care plan by the Care Manager and then the recommendation process begins automatically or by Care Manager selection.

A matrix of selected criteria is produced by the system. The system flattens and exports the model care plan into a feature hash using the matrix of selected criteria. This export process could be quite simple where there is only one value, for instance the name of a diagnosed medical illness. However if the value is in a range, such as blood pressure, the system could be made to export certain values in the range as text—"moderate blood pressure," "high blood pressure," etc. The care management system will have flattened and exported existing care plan data into feature hashes in a similar manner and these result will be available for querying. The outputs from the prior two steps are compared using a cosine similarity function to find the most similar care plans. The resulting output list may be filtered using the extra weighted criteria as chosen by the Care Manager. Care plans which have the keyword "anxiety" and also have successful goals may be ranked higher. Each care plan on this list is assigned a numeric value based on where it is in the list. This becomes the care plan recommendation score. The list of care plans is output and may be ranked by care plan recommendation score. In alternate embodiments to a full list, only a limited number (e.g., the top ten or other number) of care plans could be output or the output could just be the top scoring care plan.

The flattening and exporting process mentioned above could be completed, for example, as follows. Care plans may generally be stored in a set of well-defined database tables with specific relevant columns, e.g., blood pressure, age, date of birth etc. To create a model care plan, a Care Manager could specify columns from the set of columns available in the care plan and set a specific set of values that are relevant, for example, a specific range for blood pressure or a specific part of an address. This process could be completed, for example, using a web-based interface. These columns and appropriate values are referred to as a matrix. This matrix could also, for example, be cloned from the set of column values from an existing care plan. To create the feature hash from the matrix, all columns from the set of databases that make up a care plan are exported to simple text format such as "row name: row value." However, for the model care plan, the only row values added are the non-weighted values selected by the Care Manager as relevant. All other values can be blank. This export process could be made as complex or as simple as necessary. For example, if the value is in a range, such as blood pressure, the system could be made to export certain values in the range as text—"moderate blood pressure," "high blood pressure" etc. This example is kept simple for demonstration purposes. See Table 1. The matrix of the non-weighted Care Manager criteria selected will then be concatenated into a string and transformed into a feature hash. It is suggested that this step will use standard NLU tools for tagging and stemming the resulting string as an approximate method for grouping words with a similar basic meaning together. This will create a sparse vector as shown in Table 2. Only the non-weighted feature values will have a value. The model care plan is then stored in a database table. The non-weighted feature values are stored as the feature vector. The weighted feature values are stored in the model care plan table as SQL snippets that can be used as extra criteria in the comparison, each with their own assigned weighting factor. These are discussed in more detail below. All of the care plans in the database may be exported to feature hashes on a regular basis, for example in a nightly batch job, and the resulting feature hash is stored in a row on the care plan database. The difference from these values and the model care plan value is that all row values are added, not just a selected set of non-weighted values. This gives a fuller feature vector than the one stored against a model care plan.

One example of a comparison algorithm is provided. The model care plan is selected and a care plan comparison is started. The system loads and compares all stored care plans feature vectors to the model care plan feature vector using a cosine similarity. This will generally give a value between 0 and 1 with a higher value being more similar. The cosine similarity was chosen as it is generally quite fast over sparse vectors such as feature hashes. The weighted values stored against the model care plan are now used as extra SQL criteria to select against all care plans. If these values are found in a care plan, e.g., the medical case notes contain the word "anxiety," then the associated weight value is added to the care plan. A running total for the total weight will be kept for each care plan. The total weight score for each care plan is added to the cosine similarity value for the care plan. All care plans are ranked by this total. The place in the listing becomes the care plan recommendation score.

TABLE 1

| Column Name | Value | Weighting Factor |
| --- | --- | --- |
| Blood Pressure | 150/90 | None |
| City | Dublin | None |
| Medical Diagnosis | Dementia | None |
| Medical Case Notes | Contains word "anxiety" | 100 |
| Successful Outcome | Yes | 150 |

TABLE 2

| String | Feature Hash |
| --- | --- |
| Blood Pressure: 150/90, City: Dublin, Medical Diagnosis: Dementia | (0, 0, 0, 12, 39, 0, 0, 8) |

In a first aspect, disclosed above is a computer-implemented method of finding care plan(s) matching desired aspects. The computer-implemented method includes: receiving a selection of a model care plan from a user; generating a feature hash vector representing the model care plan, resulting in a model feature hash vector; comparing feature hash vectors of existing care plans to the model feature hash vector to find care plan(s) best matching desired aspect(s) of the user, resulting in best match(es); and providing one or more care plan recommendation to the user based on the best match(es).

In one example, the computer-implemented method may further include, for example, modifying, by the user, at least one of the best match(es).

In one example, the computer-implemented method of the first aspect may further include, for example, exporting the care plan as a flat text file, generating the feature hash vector includes generating the feature hash vector based on the flat text file. In one example, the computer-implemented method may further include, for example, applying Natural Language Understanding (NLU) to the flat text file, resulting in NLU output, generating the feature hash vector includes generating the feature hash vector from the NLU output.

In one example, the comparing in the computer-implemented method of the first aspect may include, for example, using a cosine similarity function.

In one example, the computer-implemented method of the first aspect may further include, for example, filtering the best match(es). In one example, the comparing may include, for example, using a cosine similarity function, and the filtering may include filtering one or more result of the comparing.

In one example, the computer-implemented method of the first aspect may further include, for example, assigning a recommendation score to each of the best match(es).

In one example, the selection in the computer-implemented method of the first aspect may include, for example, a shell model care plan with the desired aspect(s). In one example, at least one of the desired aspects has an assigned weight.

In a second aspect, disclosed above is a system for finding one or more care plan matching desired aspects. The system includes: a memory; and processor(s) in communication with the memory, the memory storing program code executable by the processor(s) to perform a method. The method includes: receiving a selection of a model care plan from a user; generating a feature hash vector representing the model care plan, resulting in a model feature hash vector; comparing feature hash vectors of existing care plans to the model feature hash vector to find care plan(s) best matching desired aspect(s) of the user, resulting in best match(es); and providing one or more care plan recommendation to the user based on the best match(es).

In one example, the system of the second aspect may further include, for example, exporting the care plan as a flat text file, generating the feature hash including generating the feature hash vector based on the flat text file. In one example, the system may further include, for example, applying Natural Language Understanding (NLU) to the flat text file, resulting in NLU output, generating the feature hash vector includes generating the feature hash vector from the NLU output.

In one example, the comparing in the system of the second aspect may include, for example, using a cosine similarity function.

In one example, the method of the system of the second aspect may further include assigning a recommendation score to each best match.

In a third aspect, disclosed above is a computer program product for finding one or more care plan matching desired aspects. The computer program product includes: a computer readable storage medium readable by a processor and storing instructions executable by the processor for performing a method of scheduling a meeting. The method includes: receiving a selection of a model care plan from a user; generating a feature hash vector representing the model care plan, resulting in a model feature hash vector; comparing feature hash vectors of existing care plans to the model feature hash vector to find care plan(s) best matching desired aspect(s) of the user, resulting in best match(es); and providing one or more care plan recommendation to the user based on the best match(es).

In one example, the system of the second aspect may further include, for example, exporting the care plan as a flat text file, generating the feature hash including generating the feature hash vector based on the flat text file. In one example, the system may further include, for example, applying Natural Language Understanding (NLU) to the flat text file, resulting in NLU output, generating the feature hash vector includes generating the feature hash vector from the NLU output.

In one example, the comparing in the system of the second aspect may include, for example, using a cosine similarity function.

In one example, the method of the system of the second aspect may further include assigning a recommendation score to each best match.

Figure 4:
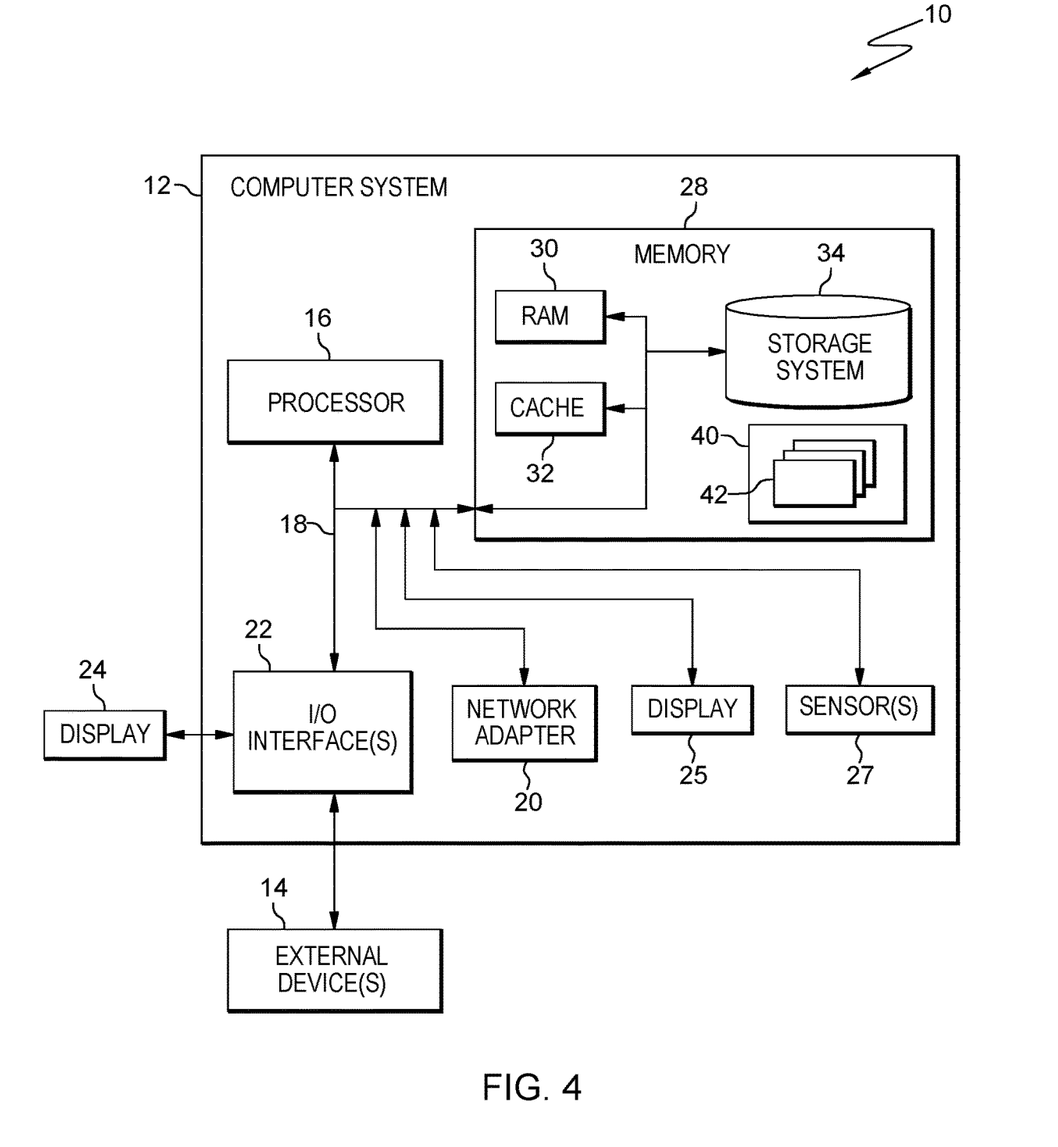
FIG. 4 is a block diagram of one example of a computer system, in accordance with one or more aspects of the present disclosure.
Figure 5:
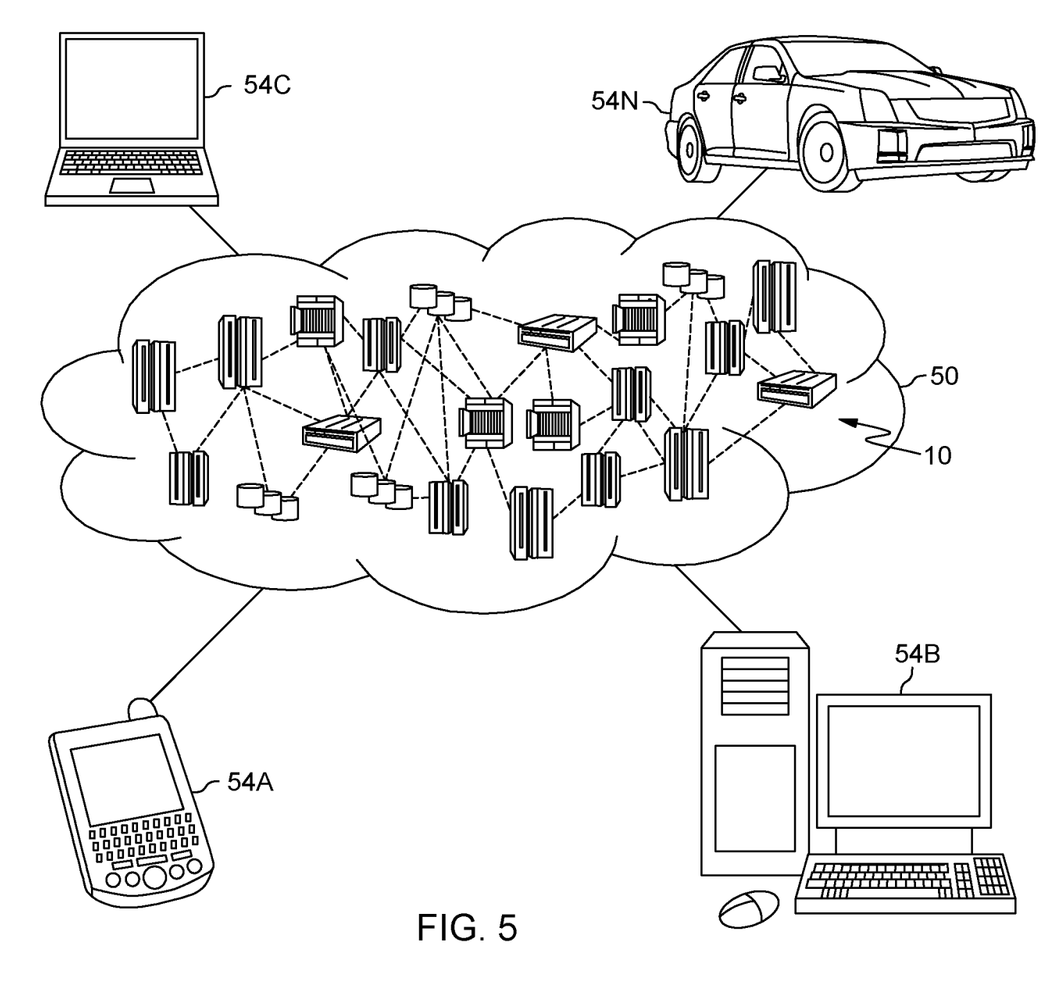
FIG. 5 is a block diagram of one example of a cloud computing environment, in accordance with one or more aspects of the present disclosure.
Figure 6:
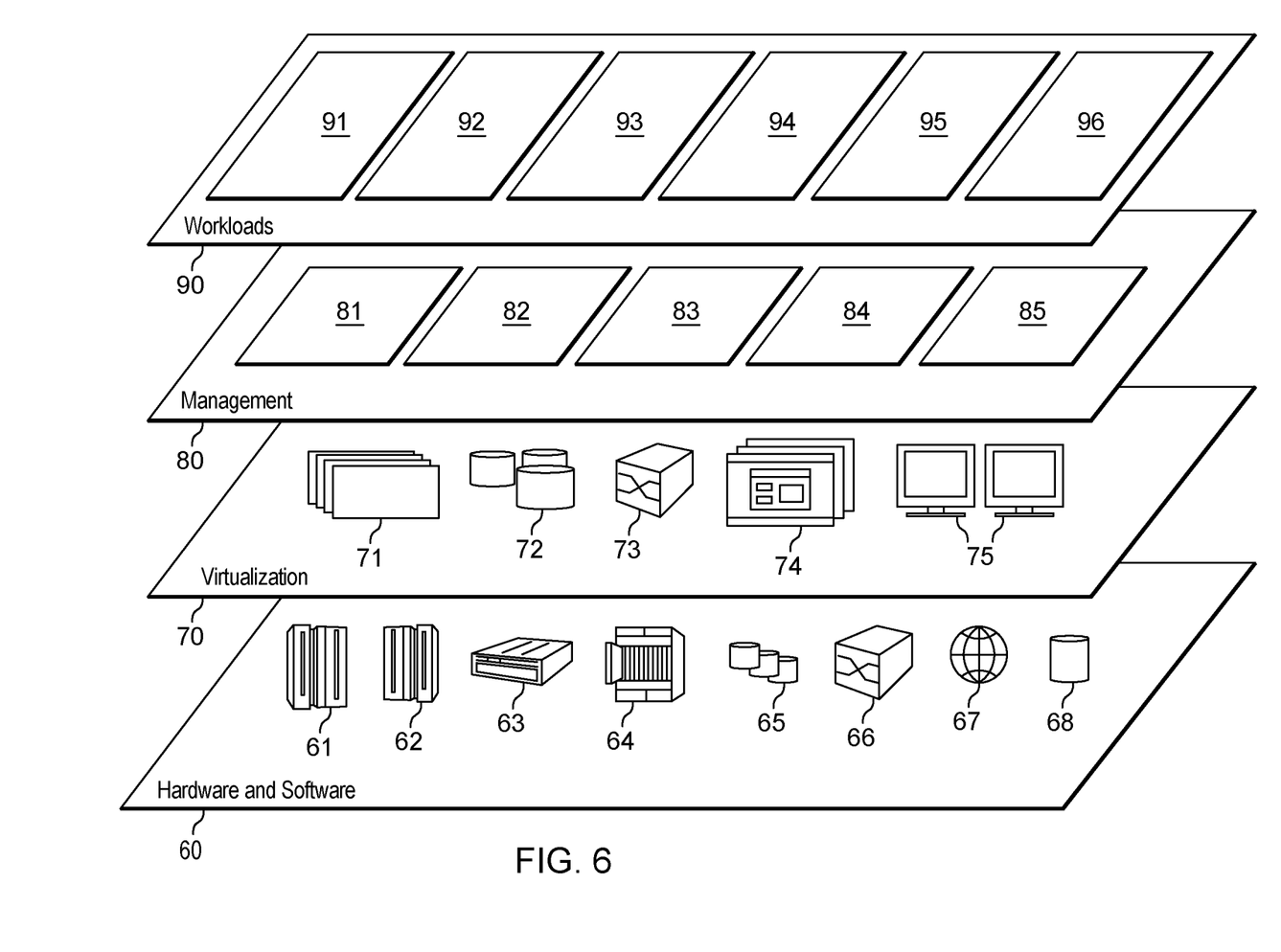
FIG. 6 is a block diagram of one example of functional abstraction layers of the cloud computing environment of FIG. 5, in accordance with one or more aspects of the present disclosure.

FIGS. 4-6 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 4, a schematic of an example of a computing node is shown. Computing node 10 is only one example of a computing node suitable for use as a cloud computing node and is not intended to suggest any limitation as to the scope of use or functionality of embodiments of the invention described herein. Regardless, computing node 10 is capable of being implemented and/or performing any of the functionality set forth hereinabove. Computing node 10 can be implemented as a cloud computing node in a cloud computing environment, or can be implemented as a computing node in a computing environment other than a cloud computing environment.

In computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system. Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 4, computer system 12 in computing node 10 is shown in the form of a computing device. The components of computer system 12 may include, but are not limited to, one or more processor 16, a system memory 28, and a bus 18 that couples various system components including system memory 28 to processor 16. In one embodiment, computing node 10 is a computing node of a non-cloud computing environment. In one embodiment, computing node 10 is a computing node of a cloud computing environment as set forth herein in connection with FIGS. 5-6.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. One or more program 40 including program processes 42 can generally carry out the functions set forth herein. One or more program 40 including program processes 42 can define machine logic to carry out the functions set forth herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc. In addition to or in place of having external devices 14 and display 24, which can be configured to provide user interface functionality, computing node 10 in one embodiment can include display 25 connected to bus 18. In one embodiment, display 25 can be configured as a touch screen display and can be configured to provide user interface functionality, e.g. can facilitate virtual keyboard functionality and input of total data. Computer system 12 in one embodiment can also include one or more sensor device 27 connected to bus 18. One or more sensor device 27 can alternatively be connected through I/O interface(s) 22. One or more sensor device 27 can include a Global Positioning Sensor (GPS) device in one embodiment and can be configured to provide a location of computing node 10. In one embodiment, one or more sensor device 27 can alternatively or in addition include, e.g., one or more of a camera, a gyroscope, a temperature sensor, a humidity sensor, a pulse sensor, a blood pressure (bp) sensor or an audio input device. Computer system 12 can include one or more network adapter 20. In FIG. 5 computing node 10 is described as being implemented in a cloud computing environment and accordingly is referred to as a cloud computing node in the context of FIG. 5.

Referring now to FIG. 5, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components 96 for establishing and updating geofence locations as set forth herein. The processing components 96 can be implemented with use of one or more program 40 described in FIG. 4.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Forms of the term "based on" herein encompass relationships where an element is partially based on as well as relationships where an element is entirely based on. Methods, products and systems described as having a certain number of elements can be practiced with less than or greater than the certain number of elements. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer-implemented method of finding one or more care plan matching desired aspects, the computer-implemented method comprising:
   receiving a selection of a model care plan from a user;
   generating a feature hash vector representing the model care plan, resulting in a model feature hash vector;
   comparing feature hash vectors of a plurality of existing care plans to the model feature hash vector to find one or more care plan best matching one or more desired aspect of the user, resulting in one or more best match; and
   providing one or more care plan recommendation to the user based on the one or more best match.

2. The computer-implemented method of claim 1, further comprising modifying, by the user, at least one of the one or more best match.

3. The computer-implemented method of claim 1, further comprising exporting the care plan as a flat text file, wherein generating the feature hash vector comprises generating the feature hash vector based on the flat text file.

4. The computer-implemented method of claim 3, further comprising applying Natural Language Understanding (NLU) to the flat text file, resulting in NLU output, wherein generating the feature hash vector comprises generating the feature hash vector from the NLU output.

5. The computer-implemented method of claim 1, wherein the comparing comprises using a cosine similarity function.

6. The computer-implemented method of claim 1, further comprising filtering the one or more best match.

7. The computer-implemented method of claim 6, wherein the comparing comprises using a cosine similarity function, and wherein the filtering comprises filtering one or more result of the comparing.

8. The computer-implemented method of claim 1, further comprising assigning a recommendation score to each of the one or more best match.

9. The computer-implemented method of claim 1, wherein the selection comprises a model care plan with the one or more desired aspect.

10. The computer-implemented method of claim 9, wherein at least one of the one or more desired aspect has an assigned weight.

11. A system for finding one or more care plan matching desired aspects, the system comprising:
   a memory; and
   at least one processor in communication with the memory, the memory storing program code executable by the at least one processor to perform a method, the method comprising:
      receiving a selection of a model care plan from a user;
      generating a feature hash vector representing the model care plan, resulting in a model feature hash vector;
      comparing feature hash vectors of a plurality of existing care plans to the model feature hash vector to find one or more care plan best matching one or more desired aspect of the user, resulting in one or more best match; and
      providing one or more care plan recommendation to the user based on the one or more best match.

12. The system of claim 11, wherein the method further comprises exporting the care plan as a flat text file, wherein generating the feature hash vector comprises generating the feature hash vector based on the flat text file.

13. The system of claim 12, wherein the method further comprises applying Natural Language Understanding (NLU) to the flat text file, resulting in NLU output, wherein generating the feature hash vector comprises generating the feature hash vector from the NLU output.

14. The system of claim 11, wherein the comparing comprises using a cosine similarity function.

15. The system of claim 11, wherein the method further comprises assigning a recommendation score to each of the one or more best match.

16. A computer program product for finding one or more care plan matching desired aspects, the computer program product comprising:
   a computer readable storage medium readable by a processor and storing instructions executable by the processor for performing a method of scheduling a meeting, the method comprising:
      receiving a selection of a model care plan from a user;
      generating a feature hash vector representing the model care plan, resulting in a model feature hash vector;
      comparing feature hash vectors of a plurality of existing care plans to the model feature hash vector to find one or more care plan best matching one or more desired aspect of the user, resulting in one or more best match; and
      providing one or more care plan recommendation to the user based on the one or more best match.

17. The computer program product of claim 16, wherein the method further comprises exporting the care plan as a flat text file, wherein generating the feature hash vector comprises generating the feature hash vector based on the flat text file.

18. The computer program product of claim 17, wherein the method further comprises applying Natural Language Understanding (NLU) to the flat text file, resulting in NLU output, wherein generating the feature hash vector comprises generating the feature hash vector from the NLU output.

19. The computer program product of claim 16, wherein the comparing comprises using a cosine similarity function.

20. The computer program product of claim 16, wherein the method further comprises assigning a recommendation score to each of the one or more best match.

* * * * *